United States Patent [19]

Michaelis

[11] 4,260,503
[45] Apr. 7, 1981

[54] MERCAPTAN AS AN ADDITIVE FOR LUBRICANTS

[75] Inventor: Peter Michaelis, Lindenfels, Fed. Rep. of Germany

[73] Assignee: Ciba-Geigy Corporation, Ardsley, N.Y.

[21] Appl. No.: 97,296

[22] Filed: Nov. 26, 1979

Related U.S. Application Data

[62] Division of Ser. No. 935,815, Aug. 22, 1978, Pat. No. 4,217,233.

[30] Foreign Application Priority Data

Aug. 31, 1977 [CH] Switzerland .................. 10609/77

[51] Int. Cl.³ .................. C10M 1/20; C10M 1/38; C07C 149/06; C07C 149/20
[52] U.S. Cl. .................. 252/48.6; 252/48.2; 560/152; 568/39; 568/57; 568/62
[58] Field of Search .................. 252/48.2, 48.6; 260/609 R; 560/152

[56] References Cited

U.S. PATENT DOCUMENTS

| | | | |
|---|---|---|---|
| 2,073,841 | 3/1937 | Humphreys et al. | 252/48.6 |
| 3,314,888 | 4/1967 | Matson | 560/152 X |
| 3,660,497 | 5/1972 | Priestley et al. | 260/609 R |

OTHER PUBLICATIONS

Snyder et al., J. Amer. Chem. Soc., 69, pp. 2675-2677 (1947).
Meade et al., J. Chem. Soc., pp. 1894-1895 (1948).

*Primary Examiner*—W. J. Shine
*Attorney, Agent, or Firm*—Luther A. R. Hall

[57] ABSTRACT

Epithio compounds or mercaptans of the formula I

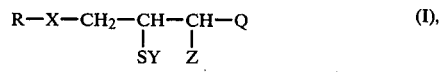

wherein X is an oxygen or sulfur atom, —CH$_2$—, —CH(R$_1$)—, —COO—, —NH— or —NR$_1$—, each of Y and Z is hydrogen or together they are a direct bond, Q is hydrogen if Y and Z together are a direct bond, or is —OH, —SH, —OR$_1$, —SR$_1$, —OOCR$_1$, —S—(CH$_2$)$_n$—OH, —S—(CH$_2$)$_n$COOR$_1$, —NHR$_1$ or —N(R$_1$)$_2$, n is an integer from 1 to 10, each of R and R$_1$ independently is a cyclic or acyclic hydrocarbon radical of aliphatic or aromatic character containing 4 to 30 carbon atoms which can be interrupted by oxygen or sulfur, with the proviso that the groups R and R$_1$ contain a total number of 8 to 30 carbon atoms. These compounds have excellent suitability for use as additives for lubricants, especially as extreme pressure and antiwear additives.

9 Claims, No Drawings

MERCAPTAN AS AN ADDITIVE FOR LUBRICANTS

This is a Divisional of application Ser. No. 935,815, filed on Aug. 22, 1978, now U.S. Pat. No. 4,217,233.

The present invention relates to $\beta$-substituted epithio compounds and adducts thereof, and to their use as additives for lubricants, in particular as extreme pressure and antiwear additives.

Compounds containing both sulfur and phosphorous, such as sulfur-containing esters of phosphoric and phosphorous acid and the use thereof as lubricant additives, have long been known in the art, cf. for example French Pat. No. 1,137,298 and Houben-Weyl, Methoden der organischen Chemie, Thieme Verlag, Vol. 12/2, pages 93–95 and 742–748.

Among the known sulfur-containing esters of phosphoric acids, representatives have been developed which constitute effective EP/AW additives for lubricants. However, these esters are not without adverse characteristics. For example, triphenylthionophosphate has in many cases only an insufficient action. The trithiophosphites, in particular the trithiophosphites from $PCl_3$ and SH-containing carboxylic acid esters described in U.S. Pat. No. 3,374,291, have a corrosive action on metal surfaces, especially at elevated temperatures. The alkyl trithio- and tetrathiophosphates proposed in U.S. Pat. No. 3,705,216 are also deficient in their effectiveness. It is held to be a drawback of the effective zinc dialkyldithiophosphates that they leave a residue on burning and therefore on account of the metal content and of the relatively low decomposition temperatures tend to form deposits, for example on contact with hot metal surfaces.

There has therefore been a need to provide oil additives which do not contain phosphorous and metal and which leave no residues on burning. Thus, for example, N-substituted fatty acid amides which contain epithio groups, for example N,N-dibutyl-9,10-epithiostearamide or N,N-dibutyl-9,10,12,13-diepithiostearamide, are described as good EP/AW additives in Chemical Abstracts 79, 1973, 94496x and 82, 1975, 88387h. Fatty acid esters containing epithio groups and terpenes with similar lubricant properties are mentioned in the journal Tribology, 3(1970), 145. A conventional method for the production of such compounds is the addition of sulfur to the double bond of olefinic fatty acid derivatives. This reaction affords the desired epithio compounds usually only in insignificant yields (cf. Chem. Rev. 66 (1966), 297). In this same publication there are described epithio compounds which are substituted by alkyl and lower alkyl ether and are obtained in good yield from the corresponding epoxides by reaction with KSCN.

Surprisingly, it has now been found that epithio compounds which are $\beta$-substituted by aryl ether or long chain alkyl ether, arylthio or long chain alkylthio ether, arylamine or long chain alkylamine, and conversion products with protonic nucleophilic reagents, are very effective lubricant additives, in particular EP/AW additives, which are superior to other products which do not contain phosphorus and contain only sulfur.

Accordingly, the present invention provides epithio compounds or mercaptans of the formula I

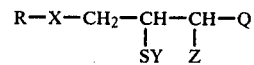

wherein X is an oxygen or sulfur atom, $-CH_2$, $-CH(R_1)-$, $-COO-$, $-NH-$ or $-NR_1-$, each of Y and Z is hydrogen or together they are a direct bond, Q is hydrogen if Y and Z together are a direct bond, or is $-OH$, $-SH$, $-OR_1$, $-SR_1$, $-OOCR_1$, $-S-(CH_2)_n OH$, $-(S-CH_2)_n COOR_1$, $-NHR_1$ or $-N(R_1)_2$, n is an integer from 1 to 10, each of R and $R_1$ independently is a cyclic or acyclic hydrocarbon radical of aliphatic or aromatic character containing 4 to 30 carbon atoms which can be interrupted by oxygen or sulfur, with the proviso that the groups R and $R_1$ contain a total number of 8 to 30 carbon atoms.

R and $R_1$ as aliphatic hydrocarbon radicals can be linear, but especially branched, alkyl of 4 to 30 carbon atoms which may be interrupted by oxygen or sulfur atoms, or cycloalkyl or cycloalkylalkyl which is unsubstituted or substituted by 1 or 2 alkyl groups of preferably 1 to 12 carbon atoms. As aromatic hydrocarbon radicals, R and $R_1$ can be aryl or aralkyl which is unsubstituted or substituted by 1 or 2 alkyl groups of 1 to 12 carbon atoms. Alkyl in this connection contains preferably 4 to 22 carbon atoms, especially 8 to 22 and most preferably 8 to 18 carbon atoms. Cycloalkyl contains 5 to 8 ring carbon atoms and is preferably cyclohexyl. Aryl is preferably phenyl and aralkyl is preferably benzyl, whilst each of cycloalkyl, phenyl or benzyl is preferably substituted by 1 or 2 alkyl groups.

In particular, R and $R_1$ in formula I are branched alkyl of 8 to 18 carbon atoms.

Examples of R are: n-butyl, isobutyl, tert-butyl, pentyl, hexyl, 2-methylpentyl, heptyl, octyl, 2-ethylhexyl, nonyl, decyl, undecyl, dodecyl, 2-ethyldecyl, tetradecyl, octadecyl, eicosyl, docosyl, tetracosyl and the isomer mixtures thereof, methoxy-n-propyl, octoxyethyl, octylthioethyl, cyclopentyl, methylcyclopentyl, ethylcyclopentylmethyl, cyclohexylmethyl, methylcyclohexyl, methylphenyl, ethylphenyl, tert-butylphenyl, dimethylphenyl, hexylphenyl, 2-ethylhexylphenyl, dinonylphenyl, dodecylphenyl, methylbenzyl, nonylbenzyl, dodecylbenzyl.

The above mentioned isomer mixtures are those which are derived from commercially available alcohols prepared via the oxo-synthesis. These products, also known as oxanols, normally consists of a mixture of branched chain, in particular primary, alcohols.

Particularly interesting epithio compounds or mercaptans are those of the formula I wherein X is an oxygen or sulphur atom or the $-COO-$ group, Y and Z have the above meanings, Q is hydrogen if Y and Z are as defined above or is $-SH$, $-SR_1$, $-S-(CH_2)_2-OH$, $-S-CH_2-COOR_1$, $-NHR_1$, and each of R and $R_1$ independently, is branched or unbranched $C_4-C_{22}$ alkyl, with the proviso that the groups R and $R_1$ contain a total number of 8 to 30 carbon atoms.

Especially preferred epithio compounds or mercaptans are those of the formula I wherein X is an oxygen atom or the $-COO-$ group, Y and Z have the above meanings, Q is hydrogen if Y and Z together are a direct bond or is $-SH$, $-SR_1$, $-S-CH_2-COOR_1$ and $-NHR_1$, and each of R and $R_1$ independently is branched $C_8-C_{22}$ alkyl, with the proviso that the groups R and $R_1$ contain a total number of 8 to 20 carbon atoms.

The most preferred epithio compounds are those of the formula II

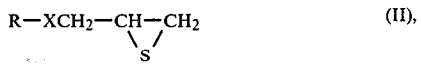

wherein R represents branched $C_8$–$C_{18}$ alkyl and X represents an oxygen atom or the —COO— group, and mercaptans of the formula III

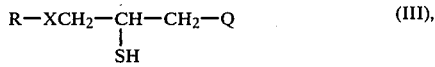

wherein X has the given meaning, Q is —$SR_1$ or —S—$CH_2$—$COOR_1$, and R and $R_1$ are branched $C_8$–$C_{18}$ alkyl, with the proviso that the groups R and $R_1$ contain a total number of 8 to 20 carbon atoms.

The epithio compounds of the invention are obtained by known methods from generally known epoxides of the formula IV

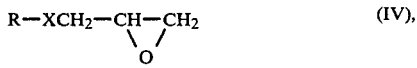

wherein R and X have the given meanings, by reaction with alkali thiocyanate or alkaline earth cyanate or thiourea. A corresponding method of manufacture is described e.g. in Org. Synth., 32(1952), 39. The above epoxides can be prepared by known methods, for example by reaction of mercaptans with epichlorohydrin, optionally in the presence of suitable catalysts.

For carrying out the reaction with thiourea, the calculated amount is suspended in approx. 10% sulfuric acid and the epoxide, dissolved in dioxan, is added dropwise with good stirring at about 0° C. to 5° C. The reaction mixture is warmed briefly to 40° C. when the dropwise addition is complete and then an approx. 20% aqueous equivalent sodium carbonate solution is added dropwise with efficient stirring. On heating to about 50° C., any precipitate which may have formed is immediately dissolved again.

To isolate the episulfides, the reaction mixture is acidified with dilute sulfuric acid and extracted repeatedly with ether. The ethereal extracts are washed neutral. The episulfides are isolated in a yield of over 90% from the ethereal solution after working up.

The mercaptans of the formula VI

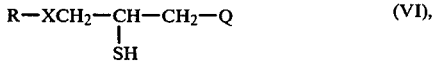

wherein R, X and Q have the given meanings, are obtained in the further reaction of the resulting epithio compounds of the formula V

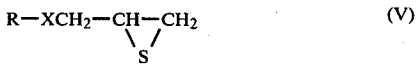

wherein R and X have the given meanings, with protonic nucleophilic reagents of the formula VII

wherein Q has the given meaning, such as alkyl mercaptans, thioglycolic acid esters or primary or secondary alkylamines. The addition of protonic nucleophilic reagents to epithio compounds is described for example in JACS 69 (1947), 2675. It is normally effected at temperatures between 50° and 150° C., preferably between 70° and 100° C., in the presence of an acid catalyst, in particular a Lewis acid, for example $BF_3$ etherate. The addition of $H_2S$ is effected by the method described in J.Chem. Soc. 1948 (3), 1894 (London).

The compounds of the present invention are liquid to viscous products which are very readily soluble in lubricants. They are pre-eminently suitable as enriching additives for lubricants, as they improve both the extreme pressure and the antiwear properties surprisingly well. In addition to this excellent action, the compounds of the invention also have very good anticorrosion and stabilizing properties.

The compounds of the formula I act even in very small amounts as extreme pressure additives in lubricants. Thus mineral and synthetic lubricant oils and mixtures thereof which contain 0.01 to 5% by weight, based on the lubricant, and preferably 0.1 to 3% by weight, of a compound of the formula I exhibit excellent extreme pressure lubricant properties which become evident from the markedly reduced signs of wear of the parts to be lubricated. The suitable lubricants are known to the skilled person and are described for example in the "Schmiermittel Taschenbuch" (Hüthig Verlag, Heidelberg, 1974).

The lubricating oil can contain still further additives which are added to improve the performance properties, such as antioxidants, metal deactivators, rust inhibitors, viscosity index improvers, pour-point depressors, dispersants/detergents. The compounds of the present invention can also be used in combination with other extreme pressure/antiwear additives.

Examples of antioxidants are (a) Alkylated and non-alkylated aromatic amines and mixtures thereof, for example: dioctyldiphenylamine, mono-tert-octyl-phenyl-α- and -β-naphthylamines, phenotriazine, dioctylphenothiazine, phenyl-α-naphthylamine, N,N'-di-sec-butyl-p-phenylenediamine.

(b) Sterically hindered phenols, for example: 2,6-di-tert-butyl-p-cresol, 4,4'-bis-(2,6-diisopropylphenol), 2,4,6-triisopropylphenol, 2,2'-thio-bis-(4-methyl-6-tert-butylphenol), 4,4'-methylene-bis-(2,6-di-tert-butylphenol) or esters of 2-(3,5-di-tert-butyl-4-hydroxyphenyl)propionic acid with e.g. hexane-1,6-diol, thiodiethylene glycol and pentaerythritol.

(c) Alkyl-, aryl- or aralkylarylphosphites, for example: trinonylphosphite, triphenylphosphite, diphenyldecylphosphite.

(d) Esters of thiodipropionic acid or thiodiacetic acid, for example: dilaurylthiodipropionate or dioctylthiodiacetate.

(e) Salts of carbamic and dithiophosphoric acids, for example: antimony diamyldithiocarbamate, zinc diamyldithiophosphate.

(f) A combination of two or more of the above antioxidants, for example: an alkylated amine and a sterically hindered phenol.

Examples of metal deactivators are (a) for copper: for example benzotriazole, tetrahydrobenzotriazole, 2-mercaptobenzotriazole, 2,5-dimercaptothiadizole, salicylidene propylenediamine, salts of salicylaminoguanidine.

(b) for lead: for example sebacic acid derivatives, quinizarine, propyl gallate.

(c) a combination of two or more of the above additives.

Examples of rust inhibitors are (a) Organic acids, the esters, metal salts and anhydrides thereof, for example: N-oleyl-sarcosine, sorbitan monooleate, lead naphthenate, dodecenylsuccinic anhydride.

(b) Nitrogen-containing compounds, for example:

I. Primary, secondary or tertiary aliphatic or cycloaliphatic amines and amine salts of organic and inorganic acids, for example oil-soluble alkylammonium carboxylates.

II. Heterocyclic compounds, for example substituted imidazolines and oxazolines.

(c) Phosphorus-containing compounds, for example: amine salts of phosphoric acid partial esters.

(d) Sulfur-containing compounds, for example: barium dinonylnaphthalenesulfonates, calcium petroleum sulfonates.

(e) Combinations of two or more of the above additives.

Examples of viscosity index inprovers are polymethylacrylates, vinyl pyrrolidone/methacrylate copolymers, polybutenes, olefin copolymers.

Examples of pour-point depressors are polymethacrylates, alkylated naphthalene derivatives.

Examples of dispersants/surfactants are polybutenylsuccinic imides, polybutenylphosphonic acid derivatives, superbasic magnesium, calcium and barium sulfonates and phenolates.

Examples of other wear-resisting additives are compounds which contain sulfur and/or phosphorus and/or halogen, such as sulfurised vegetable oils, zinc dialkyldithiophosphates, tritolylphosphate, chlorinated paraffins, alkyl- and aryldisulfides.

The following examples describe in more detail the manufacture of the lubricant additives and also their use and action in lubricants.

(A) Manufacturing Examples

EXAMPLES 1 TO 4

In accordance with the procedure described in Org. Synth. 32 (1952), 39, the epithio compound indicated in column 3 of Table I is obtained in virtually quantitative yield from the alkyl glycidyl ether of column 2 by reaction with KSCN.

TABLE I

| Example | Alkyl glycidyl ether | Epithio compound | Properties (°C.) |
|---|---|---|---|
| 1 | $H_9C_4-CH(C_2H_5)-CH_2-OCH_2CH-CH_2$ (epoxide) | $H_9C_4-CH(C_2H_5)-CH_2-OCH_2CH-CH_2$ (episulfide) | b.p. 91°/0,1 mm $n_D^{22}$: 1.4699 |
| 2 | $C_9H_{19}-C(CH_3)_2-SCH_2CH-CH_2$ (epoxide) | $C_9H_{19}-C(CH_3)_2-SCH_2CH-CH_2$ (episulfide) | b.p. 119°/0,01 mm $n_D^{22}$: 1.5049 |
| 3 | $iC_{13}H_{27}OCH_2CH-CH_2^{(1)}$ (epoxide) | $iC_{13}H_{27}OCH_2CH-CH_2$ (episulfide) | $n_D^{20}$: 1.4762 |
| 4 | $C_{12-15}H_{25-31}OCH_2CH-CH_2^{(2)}$ (epoxide) | $C_{12-15}H_{25-31}OCH_2CH-CH_2$ (episulfide) | $n_D^{20}$: 1.4650 |

(1) Ruhrchemie: iso-tridecanol = mixture of short chain branched alcohols (e.g. 2,5,7-trimethyl-decanol inter alia) as alcohol component
(2) "Dobanol-(25)" (supplier: Shell) as alcohol component

EXAMPLE 5

3 drops of $BF_3$ etherate are added to 0.1 mole of the thioglycolic acid ester of 2-ethylhexanol and the mixture is heated on a water bath. Then 0.05 mole of epithio-2-ethylhexyl ether is added and the reaction mixture is stirred for 1 hour at 60° C. Distillation yields the desired mercaptan of the formula

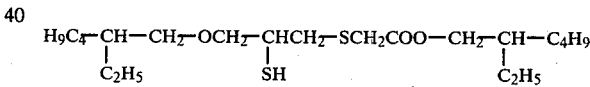

in 85% yield.

EXAMPLES 6 TO 19

Column 4 of Table II lists further mercaptans of the invention which are obtained by proceding in a manner analogous to that described in Example 3 by reaction of corresponding protonic nucleophilic reagents (column 2) with corresponding epithio compounds (column 3).

TABLE II

| Example | Protonic nucleophilic reagents | Epithio compound | Mercaptan | Properties (°C.) |
|---|---|---|---|---|
| 6 | $H_2S$ | $R'-OCH_2-CH-CH_2$ (episulfide) | $R'-OCH_2-CH(SH)-CH_2(SH)$ | b.p.: 95° C./ 0.05 mm $n_D^{22}$: 1.4825 |
| 7 | $HS-C(CH_3)_2-C_9H_{19}$ | $R'-OCH_2-CH-CH_2$ (episulfide) | $R'-OCH_2-CH(SH)-CH_2S-C(CH_3)_2-C_9H_{19}$ | $n_D^{22}$: 1.4711 |
| 8 | $H_2N-n-C_4H_9$ | $R'-OCH_2-CH-CH_2$ (episulfide) | $R'-OCH_2-CH(SH)-CH_2NH-n-C_4H_9$ | b.p.: 118-122°/ 95 torr |

TABLE II-continued

| Example | Protonic nucleophilic reagents | Epithio compound | Mercaptan | Properties (°C.) |
|---|---|---|---|---|
| 9 | HS—R''' | R'—OCH₂—CH—CH₂ \S/ | R'—OCH₂—CH(SH)—CH₂—S—R''' | $n_D^{22}$: 1.4795 |
| 10 | HS—CH₂—C(O)—O—CH₂—CH(C₂H₅)—C₄H₉ | R'—OCH₂—CH—CH₂ \S/ | R'—OCH₂—CH(SH)—CH₂—S—CH₂—C(=O)—O—CH₂—CH(C₄H₉)(C₂H₅) | $n_D^{20}$: 1.4898 |
| 11 | HS—CH₂—CH₂OH | R'—OCH₂—CH—CH₂ \S/ | R'OCH₂—CH(SH)—CH₂—S—CH₂—CH₂OH | $n_D^{20}$: 1.5012 |
| 12 | HS—R''' | C₉H₁₉—C(=O)—OCH₂—CH—CH₂ \S/ | C₉H₁₉—C(=O)—O—CH(SH)—CH₂—S—R''' | $n_D^{20}$: 1.4782 |
| 13 | HS—R''' | R''—OCH₂—CH—CH₂ \S/ | R''—OCH₂—CH(SH)—CH₂—S—R''' | $n_D^{20}$: 1.4808 |
| 14 | HS—R''' | R'ⱽ—OCH₂—CH—CH₂ \S/ | R'ⱽ—OCH₂—CH(SH)—CH₂—S—R''' | $n_D^{20}$: 1.4843 |
| 15 | H₂S | R'ⱽ—OCH₂—CH—CH₂ \S/ | R'ⱽ—OCH₂—CH(SH)—CH₂(SH) | $n_D^{20}$: 1.4830 |
| 16 | H₂S | R'''—SCH₂—CH—CH₂ \S/ | R'''—SCH₂—CH(SH)—CH₂(SH) | $n_D^{20}$: 1.5190 |
| 17 | HS—R''' | R'''—SCH₂—CH—CH₂ \S/ | R'''—SCH₂—CH(SH)—CH₂—S—R''' | $n_D^{20}$: 1.4991 |
| 18 | HS—CH₂—C(=O)—O—CH₂—CH(C₂H₅)—C₄H₉ | R'''—SCH₂—CH—CH₂ \S/ | R'''—SCH₂—CH(SH)—CH₂—S—CH₂—C(=O)—O—CH₂—CH(C₄H₉)(C₂H₅) | $n_D^{20}$: 1.5032 |
| 19 | HS—CH₂—CH₂—OH | R'''—SCH₂—CH—CH₂ \S/ | R'''—SCH₂—CH(SH)—CH₂—S—CH₂—CH₂OH | $n_D^{20}$: 1.5240 |

$R' = -CH_2-CH(C_2H_5)-C_4H_9$ $R'' =$ mixture of alkyl groups containing 12–15 carbon atoms [starting from $C_{12-15}H_{25-31}OH$ "Dobanol-(25)" (Shell)]

$R''' = -C(CH_3)_2-C_9H_{19}$ $R'ⱽ =$ mixture of isomeric branched chain $C_{13}$-alkyl groups [starting from isotridecanol (Ruhrchemie)]

(B) Application Examples

The following values were determined with a four ball tester for lubricating oils: (Tentative method IP 239/69; extreme pressure and wear lubricant test for oils and greases, four ball machine).

(1) W.L. = weld load, i.e. the load at which the oil film breaks up within a period of 10 seconds.

(2) W.S.D. = wear scar diameter in mm, i.e. the average wear diameter at a load of 70 kg in the course of 1 hour.

(3) In all cases the corrosive action was tested in the copper strip test (CST). The rating is from 1a to 4b.

Catenax 41 (registered trademark of Shell) was used as base oil. The results are reported in Table III.

TABLE III

| Additive | Concentration | Weld load (kg) | Scar diameter (mm) | CST |
|---|---|---|---|---|
| — | — | 160 | 2.42 | — |
| Example 1 | 1% | >200 | 0.6 | 1a |
| Example 2 | 1% | >200 | 0.8 | 1a |
| Example 3 | 1% | >200 | 0.5 | 1a |
| Example 4 | 1% | >200 | 0.5 | 1a |
| Example 5 | 1% | >200 | 0.6 | 1a |
| Example 7 | 1% | >200 | 0.5 | 1b |
| Example 9 | 1% | >180 | 0.4 | 1b |
| Example 10 | 1% | >200 | 0.3 | 1a |
| Example 11 | 1% | >200 | 0.6 | 1a |
| Example 12 | 1% | >180 | 0.5 | 1a |
| Example 13 | 1% | >180 | 0.4 | 1a |
| Example 14 | 1% | >180 | 0.5 | 1a |
| Example 15 | 1% | >200 | 0.7 | 1a |

| Additive | Concentration | Weld load (kg) | Scar diameter (mm) | CST |
|---|---|---|---|---|
| Example 16 | 1% | >200 | 1.1 | 2b |
| Example 17 | 1% | >180 | >1.2 | 1a |
| Example 18 | 1% | >200 | 0.7 | 2c |
| Example 19 | 1% | >200 | 0.7 | 2e |

What is claimed is:

1. A mercaptan of the formula

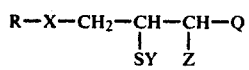

wherein

X is an oxygen or sulfur atom or the —COO— group,

Y and Z are each hydrogen, and

Q is —SH, —SR$_1$ or —S—CH$_2$—COOR$_1$, each of R and R$_1$ independently is branched or unbranched C$_4$–C$_{22}$ alkyl, with the proviso that the groups R and R$_1$ contain a total number of 8 to 30 carbon atoms.

2. A mercaptan according to claim 1 of the formula I, wherein X is an oxygen atom or the —COO— group, Y and Z are as defined in claim 1, Q is —SH, —SR$_1$ or —S—CH$_2$—COOR$_1$, and each of R and R$_1$ independently is C$_8$–C$_{22}$ alkyl, with the proviso that the groups R and R$_1$ contain a total number of 8 to 20 carbon atoms.

3. A mercaptan according to claim 1 of the formula

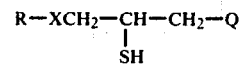

wherein X is an oxygen atom or the —COO— group, Q is —SR$_1$ or —S—CH$_2$—COOR$_1$, and R and R$_1$ are branched C$_8$–C$_{18}$ alkyl, with the proviso that the groups R and R$_1$ contain a total number of 8 to 20 carbon atoms.

4. A mercaptan according to claim 1 of the formula wherein R and R$_1$ are C$_8$–C$_{22}$ alkyl.

5. A mercaptan according to claim 1 of the formula wherein R and R$_1$ are C$_8$–C$_{18}$ alkyl.

6. A mercaptan according to claim 1 of the formula

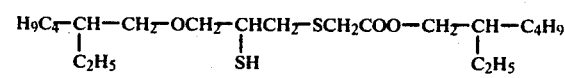

7. A mercaptan according to claim 1 of the formula

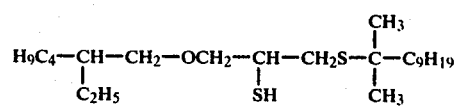

8. A composition of matter containing a mineral or synthetic lubricant or mixture thereof and an effective amount of a compound of the formula according to claim 1.

9. A process for stabilizing lubricant compositions which comprises adding an effective amount of a mercaptan compound according to claim 1.

* * * * *